(12) United States Patent
Kuhn

(10) Patent No.: US 7,416,410 B2
(45) Date of Patent: Aug. 26, 2008

(54) MEDICAL OR DENTAL HANDPIECE WITH A REAR AND A FRONT SHAFT SECTION THAT FORM AN OBTUSE ANGLE

(75) Inventor: Bernhard Kuhn, Biberach (DE)

(73) Assignee: Kaltenbach & Voigt GmbH & Co. KG, Biberach (DE)

( * ) Notice: Subject to any disclaimer, the term of this patent is extended or adjusted under 35 U.S.C. 154(b) by 387 days.

(21) Appl. No.: 10/488,348

(22) PCT Filed: Aug. 9, 2002

(86) PCT No.: PCT/EP02/08932

§ 371 (c)(1),
(2), (4) Date: Oct. 29, 2004

(87) PCT Pub. No.: WO03/020149

PCT Pub. Date: Mar. 13, 2003

(65) Prior Publication Data

US 2005/0089817 A1    Apr. 28, 2005

(30) Foreign Application Priority Data

Aug. 28, 2001 (EP) .................................. 01120523
Feb. 28, 2002 (DE) ................................. 102 08 691

(51) Int. Cl.
*A61C 1/02* (2006.01)
*A61C 1/12* (2006.01)

(52) U.S. Cl. .................. 433/105; 433/114; 433/133
(58) Field of Classification Search ................. 433/133, 433/105, 114; 74/63
See application file for complete search history.

(56) References Cited

U.S. PATENT DOCUMENTS 3,229,369 A * 1/1966 Hoffmeister et al. ........ 433/105

(Continued)

FOREIGN PATENT DOCUMENTS

DE        93 07 903.6        9/1993

(Continued)

OTHER PUBLICATIONS

International Preliminary Examination Report in PCT/EP02/08932 dated Dec. 5, 2003.

*Primary Examiner*—John J Wilson
(74) *Attorney, Agent, or Firm*—Marshall, Gerstein & Borun LLP

(57) ABSTRACT

The invention relates to a medical or dental medical handpiece (3) having an elongate shaft (13), which has in its front end region a tool holder (5) having a lateral insertion opening (5a) for a tool (6), and having a rearward and a forward shaft section (13a, 13b) which include an obtuse angle (W2) which is open to the side away from the insertion opening (5a), wherein in the shaft sections (13a, 13b) there is rotatably mounted in each case a drive shaft section (53a, 53c), which stand in driving connection with one another by means of gears meshing with one another, and wherein the forward shaft section (13b) stands in driving connection with the tool holder (5) by means of gears (58, 59) meshing with one another. In order to improve handling, the angle (W3) include between the middle axis (16) of the insertion opening (5a) and the middle axis (13e) of the forward shaft section (13b) is greater than 90° and the forward gear (58) of the forward drive shaft section (53c) meshes on its side away from the insertion opening (5a) with the gear (59) of the tool holder (5).

8 Claims, 3 Drawing Sheets

U.S. PATENT DOCUMENTS

Figure 1:
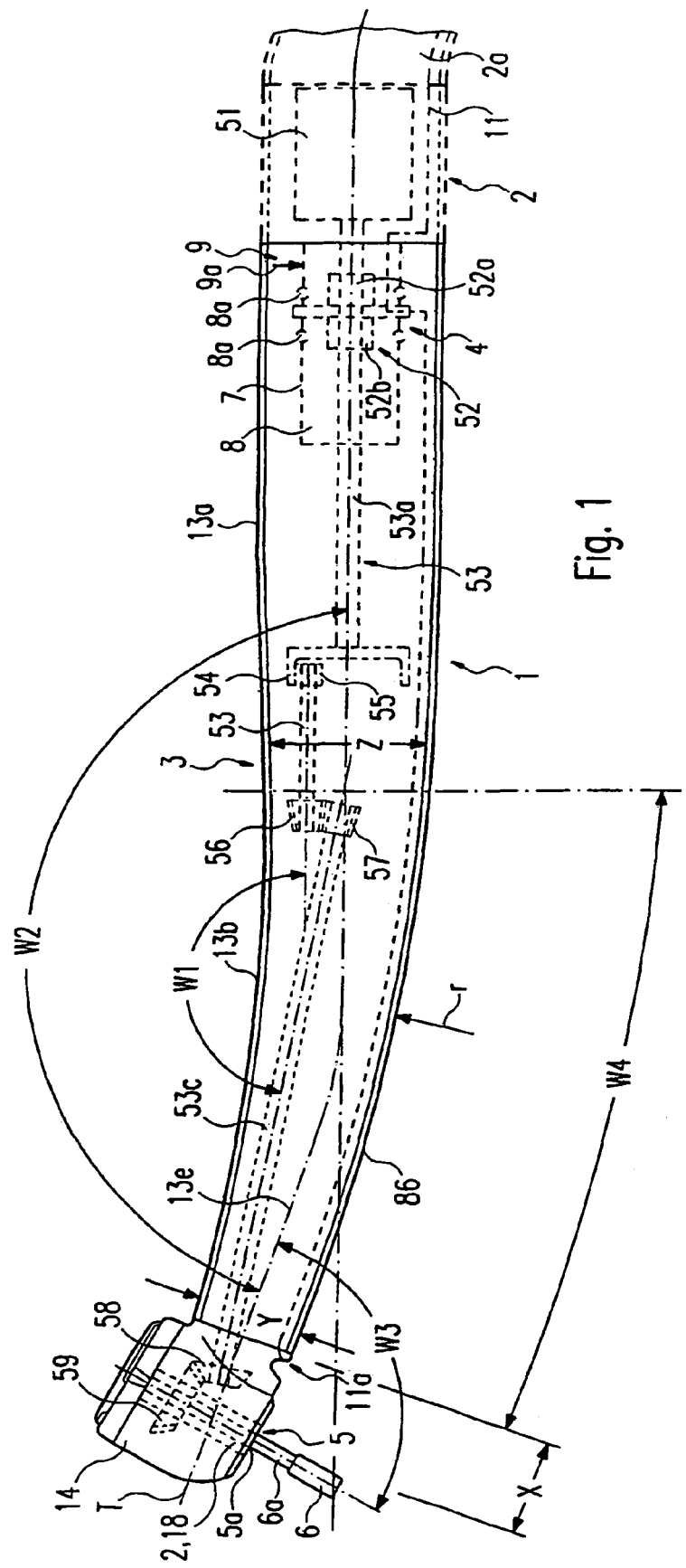

| | | | | |
|---|---|---|---|---|
| 4,276,025 A | * | 6/1981 | Straihammer | 433/105 |
| 4,278,428 A | | 7/1981 | Straihammer et al. | 433/105 |
| 4,325,696 A | * | 4/1982 | Rosenstatter et al. | 433/133 |
| 4,493,646 A | * | 1/1985 | Lacour et al. | 433/133 |
| 4,568,642 A | * | 2/1986 | DeForrest et al. | 433/132 |
| 4,693,685 A | | 9/1987 | Pernot | 433/105 |
| 5,575,647 A | * | 11/1996 | Grubbs | 433/114 |
| 5,584,689 A | | 12/1996 | Loge | 433/128 |
| 6,638,068 B2 | * | 10/2003 | Lingenhole et al. | 433/114 |

FOREIGN PATENT DOCUMENTS

| | | |
|---|---|---|
| DE | 44 08 574 A1 | 2/1995 |
| DE | 198 48 556 A1 | 4/2000 |
| EP | 185 400 B1 | 6/1986 |
| FR | 2 336 590 | 7/1977 |
| FR | 2 522 493 | 9/1983 |

* cited by examiner

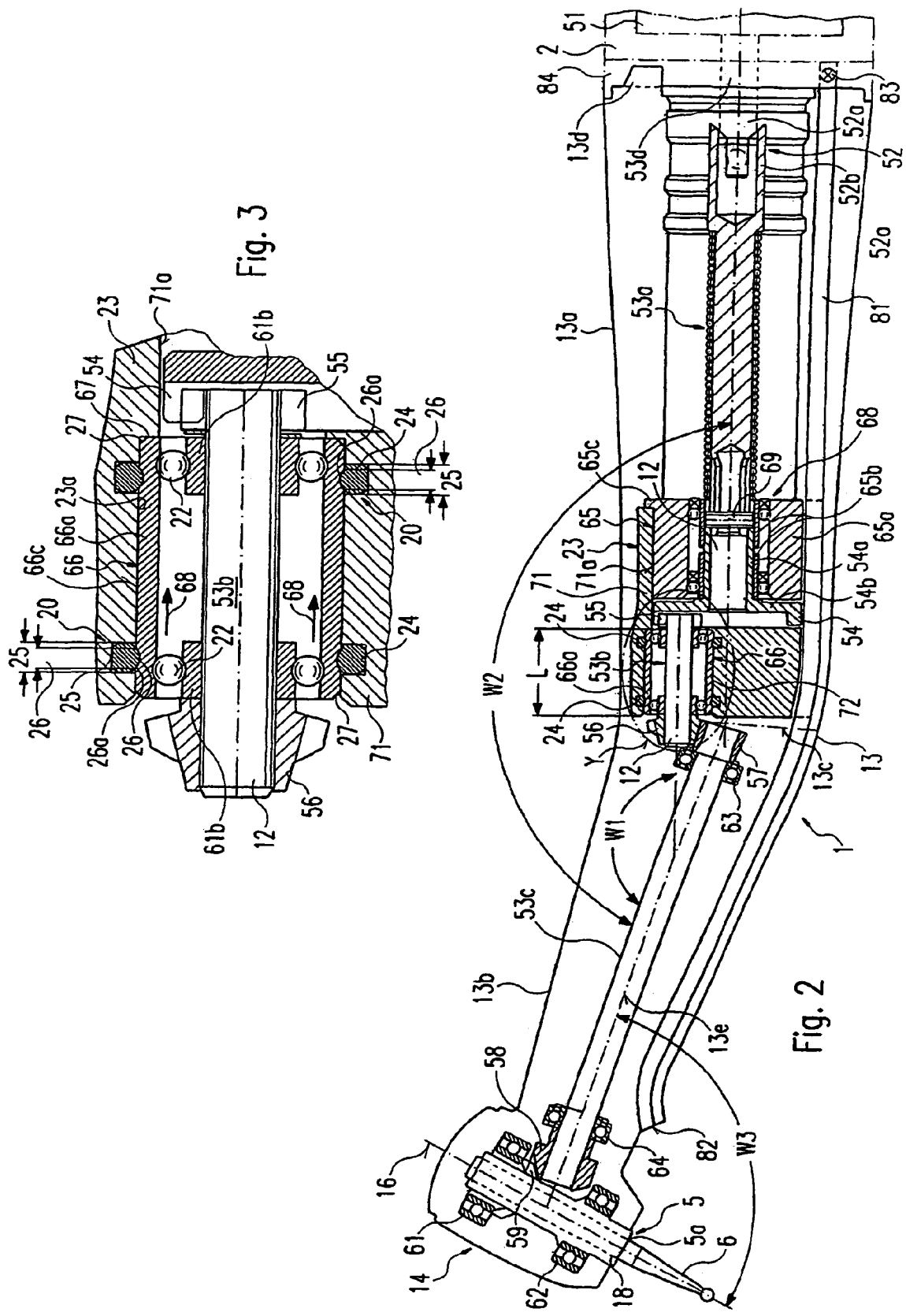

MEDICAL OR DENTAL HANDPIECE WITH A REAR AND A FRONT SHAFT SECTION THAT FORM AN OBTUSE ANGLE

This is the U.S. national phase of International Application No. PCT/EP02/08932 filed Aug. 9, 2002, the entire disclosure of which is incorporated herein by reference.

The invention relates to a medical or dental-medical handpiece according to the preamble of claim 1 or 5.

A medical or dental-medical handpiece is an object which is put to use for working the human body or natural or artificial parts thereof, such as prostheses, with a tool. The tool is in most configurations a material removing tool which acts on the body with a rotational movement or with a movement going back and forth. As drive there serves a rotational motor which may be arranged in the handpiece itself or in a so-called connection part with which the handpiece is releasably connected by means of a plug-in, in particular a plug-in/turn coupling having a coupling recess in one the one part and a coupling pin, engaging the coupling recess, on the other part. Also in the presence of a back and forth going tool drive, the drive movement is derived from a rotary movement which at least one rotary part carries out and for this purpose is rotatably mounted in the inner ring of a roller bearing having the inner ring and an outer ring. For axially positioning the inner ring and/or the outer ring of a roller bearing it is usual to provide shoulder surfaces on which the roller bearing ring concerned bears and thus is restricted against an axial movement.

In the case of a dental medical handpiece described in DE 44 08 574 A1 (see in particular FIGS. 1 and 2 of this document), the drive shaft section rotatably mounted in the forward shaft section is drivingly connected with the tool holder by means of a herringbone gear transmission, which tool holder is formed by means of a receiving sleeve rotatably mounted and extending transversely to the shaft, on which the associated herringbone gear meshes with the herringbone gear on the forward drive shaft section on its side towards the insertion opening. The angle included between the middle axis of the tool holder and the middle axis of the forward shaft section is about 90°. The forward drive shaft section and a non-illustrated rearward drive shaft section are connected with one another by means of a herringbone gear transmission, the gears of which have teeth on their sides towards one another which stand in engagement with one another.

From EP 0 185 400 B1 there can also be understood a handpiece as described above, which in accordance with FIG. 2 has in the apex region of an angling a drive shaft section which is connected in each case by means of a herringbone gear transmission with a rearward drive shaft section and a forward drive shaft section, and which extends obliquely from the rear forwardly between the rearward and the forward drive shaft section.

In the publication DE 93 07 903 U1 there is described a dental medical handpiece having an angled handpiece shaft, in which there are rotatably mounted a rearward drive shaft section, a middle drive shaft section and a forward drive shaft section. The middle drive shaft section is, with regard to the rearward drive shaft section, arranged offset towards the side away from the tool, and it has at its forward end, which is located in the bend region of the handpiece, a hollow gear which meshes with a rearward gear on the forward drive shaft section in such a manner that the latter meshes with the hollow gear of the middle drive shaft section on its side towards the tool.

With such a handpiece in which there is rotatably mounted, for the drive of the tool holder, a drive shaft of a plurality of drive shaft sections there arise particular demands in particular in the region of the apex of a handpiece angled or curved to the side, taking into account desired speeds of rotation and/or directions of rotation, whereby here also a compact construction is to be striven for in order to obtain a simple construction in the restricted space of a handpiece.

The invention thus has the object of improving a medical or dental medical handpiece with regard to the effectiveness of the drive shaft sections standing in driving connection with one another.

With a configuration in accordance with one embodiment of the invention, the rear gear of the forward drive shaft section on its side away from the insertion opening for the tool meshes with the gear of the rearward drive shaft section on the side towards the insertion opening. This configuration leads not only to a simple and robust construction, but it makes possible in comparison with known drive connections a reversal of direction of rotation, which may be desired for various reasons. For example, a further middle drive shaft section may be provided which makes it possible to reverse the direction of rotation of the forward drive shaft section and/or to bring about stepping up of the speed of rotation or stepping down of the speed of rotation. Through this, the handpiece can be so altered that it can fulfill specific or a large range of demands and thus the range of applications of the handpiece can be increased.

A medical or dental-medical handpiece according to another embodiment of the invention is described in U.S. Pat. No. 4,278,428 A. Here there is involved a dental drill handpiece of curved form with a tool which can be inserted from the side, whereby there extends in the shaft of the handpiece a drive train of a plurality of the drive shaft sections. A rearward drive shaft section, extending up to the beginning region of the curvature, and a forward drive shaft section extending therefrom forwardly, stand in engagement with one another by means of a gear transmission, whereby the rearward gear of the forward drive shaft section meshes, on its side away from the tool, with the associated gear of the rearward drive shaft section (see exemplary embodiment according to FIG. 10).

In the case of a handpiece for or with a tool which in functional operation rotates at high speed, improvement is needed with regard to the noise caused thereby, to the effect that the running noise is reduced or avoided, since a noisy operation is disturbing both for the person carrying out the treatment and also for the patient. This applies in particular for handpieces which are used in the head region of the patient as is the case with dental medical handpieces.

The invention thus also has the object of so configuring a medical or dental medical handpiece that a low noise operation and/or a simple and stable construction is attained.

A handpiece in accordance with this embodiment of the invention has, for mounting the tool holder, a roller bearing with at least two roller body rows arranged next to one another, which are located to both sides of the forward gear of the drive shaft, whereby the latter or the gear arranged thereon radially passes through the outer sleeve of the roller bearing in a through-hole.

A configuration in accordance with this embodiment of the invention leads to a reduction of the running noise. This can be attributed to the fact that a common roller bearing outer sleeve is present which makes possible a stabilised support in the head of the handpiece, which leads to a reduction of the running noise. Thus, this configuration in accordance with the invention is in particular suitable for a handpiece for or with a tool which rotates at high speed in functional operation, as is the case with high speed motor handpieces or turbine handpieces. This configuration in accordance with the invention is suitable, however, also for low speed handpieces, whereby the other above-mentioned advantages can be attained.

Through this configuration, the construction is simplified, because only one roller bearing is needed for mounting the tool holder. Through this not only is the number of necessary individual components reduced, but also the effort needed for installation or de-installation, since only one roller bearing needs to be installed or de-installed.

With regard to its readiness of handling at the site of treatment, high demands are made of a handpiece of the kind concerned here. This because in many cases there is to be carried out work which is on the one hand fine and on the other hand precise. Here, for ergonomic reasons, there are to be striven for a handling-friendly construction of the handpiece and a handling-friendly position of the handpiece during the treatment or operation, so that the operating person can direct their attention less to the handpiece and more to the site of operation.

Through further development of the handpiece it has been striven for to improve its handling. This is achieved by means of another embodiment of the invention.

With this embodiment, the middle axis of the forward shaft section and the middle axis of the insertion opening include an angle which is greater than 90° and which is open towards the tool side of the handpiece. Further, the gear arranged at the forward end of the forward drive shaft section meshes on its side away from the tool side of the handpiece with the corresponding gear of the tool holder. Through this the handpiece is given a structural form which makes possible an ergonomically favourable holding of the handpiece with the operating hand, and thus places the operating person in the position of directing their attention less to the manual grasping of the handpiece and more to the treatment or operational procedures. The configuration in accordance with the invention is particularly suitable for a dental medical handpiece, because it is better adapted to the anatomy in the mouth region of the patient and improves the moveability and exploitation of space in the mouth of the patient: In this regard, the invention is based on the insight that the human upper and lower jaws in each case can be opened with an angle of about 20°. In this respect, the configuration in accordance with the invention represents a median form, which makes it possible to move the handpiece in the free space present between the jaws to both sides.

This further development leads to a simple and structurally favourable construction, which is suitable both for a so-called angled handpiece and also for a handpiece curved to the side in the forward region, whereby it is to be taken into account that in particular for a dental medical handpiece the structural size is restricted and therefore a compact structure is striven for, which the configuration in accordance with the invention makes possible.

In comparison with the generic configuration indicated in the introduction, the configuration in accordance with the invention leads to a reversal of direction of rotation for the tool holder or the tool, whereby the reversal of direction of rotation is compensated and thus a drive can be used which is unchanged with regard to the direction of rotation.

The configuration in accordance with the invention is suitable both for a rearward and a forward drive shaft section and also for an additional middle or third drive shaft section which with respect to the middle axis of the rearward drive shaft section may extend parallel or obliquely thereof.

Further features of the subclaims make possible a favourable mounting arrangement, which both simplifies the construction of the mounting and also the installation of de-installation thereof and beyond this is of compact construction, which can be favourably arranged in the handpiece.

Further features of the subclaims make possible a simple, compact and economically producible construction, which is suitable in particular for the restricted space conditions in a handpiece of the kind concerned here. Further, there is made possible an axially effective securing for a roller bearing and a simple installation or de-installation of various components of the handpiece, in particular of the roller bearing and/or of drive shaft sections.

Below, advantageous configurations of the invention will be described in more detail with reference to exemplary embodiments and drawings.

There is shown:

FIG. 1 a handpiece in accordance with the invention, in a side view, which together with a so-called connection part forms a treatment instrument;

FIG. 2 a handpiece in accordance with the invention, in further modified configuration, in axial section;

FIG. 3 the middle region, designated by Y, of the handpiece according to FIG. 2, in axial section to an enlarged scale.

Figure 4:
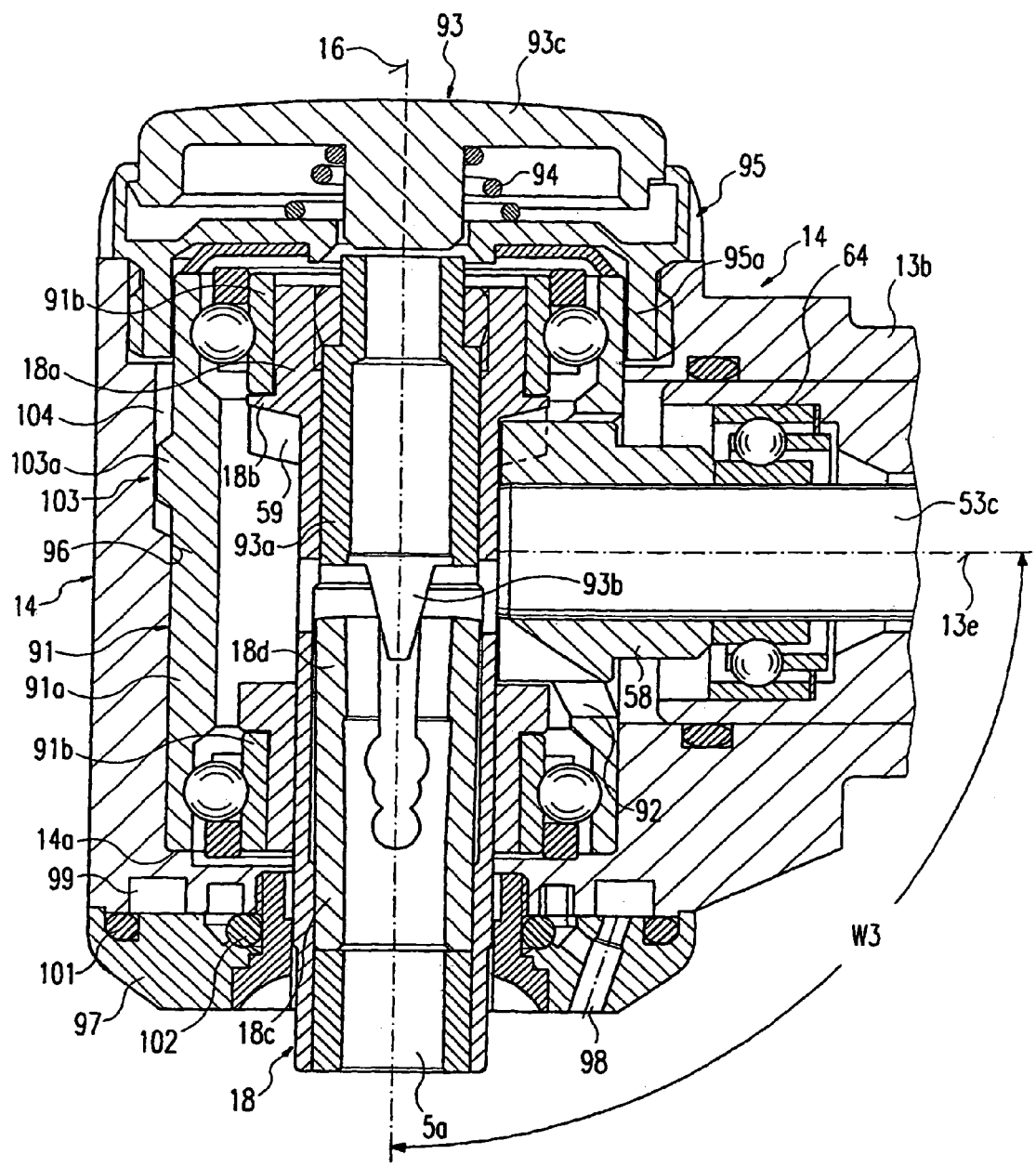

FIG. 4 the forward end region of the handpiece, in longitudinal section, in a modified configuration.

The treatment instrument, designated in its entirety by 1 in FIG. 1, consists of a rearward instrument part, namely a so-called connection part 2, and a forward instrument part, namely the so-called handpiece 3, which are releasably connected with one another by means of a coupling 4, in particular a plug-in coupling, preferably a plug-in/turn coupling. With the present exemplary embodiment there is arranged at the forward end of the treatment instrument 1 a holder device 5 having a lateral insertion opening 5a for a tool 6, whereby the tool 6 may stand out to the side or forwardly. The handpiece may extend straight (not illustrated) or curved (indicated by chain lines) to the side away from the tool 6, or angle shaped. The plug-in/turn coupling is formed by means of a coupling recess 7, round in cross-section, and in coupling pin 8 which can be inserted therein with slight play for movement. With the present exemplary embodiment, the coupling recess 7 is arranged at the rearward end of the handpiece 3, and the substantially cylindrical coupling pin 8 extends from the connection part 2 forwardly. In the coupled condition the coupling recess 7 and the coupling pin 8 are releasably latched to one another by means of a latching device 9. This has a latching element 9a which is mounted radially moveably in the one coupling part and is biassed by means of a spring force into a latching position, crossing the dividing gap, in which the latching element 9a engages into a ring groove in the other coupling part. Such a latching device 9 is self-actingly latched upon coupling and upon uncoupling can be overcome by a manual exercise of an axial pulling force, whereby the latching element 9a is self-actingly forced into its release position.

The connection part 2 is connected with a flexible supply line 2a, which is connected with a non-illustrated control apparatus. The handpiece 3 is preferably freely rotatably mounted on the coupling pin 8, through which handling is improved. Through the plug-in/turn coupling 4 there extends at least one media line 11 for a treatment or drive medium, e.g. water, compressed air, or a water/air mixture (spray). The media line 11 can extend axially through a radial dividing gap (not illustrated) or Z-shaped through a hollow cylindrical dividing gap between the coupling recess 7 and the coupling pin 8, whereby the media line 11 crosses the dividing gap in the region of a ring groove in the coupling pin 8 or in the coupling recess 7, so that in any rotary position the passage of media is ensured. To both sides of the passage, the dividing gap is sealed by means of a sealing ring 8a which may be arranged in a ring groove in the wall of the coupling recess 7 or in the outer surface of the coupling pin 8. Through this a free rotatability through 360° and more is ensured. The media line 11 extends from the rearward end of the treatment instrument 1 to its forward end region, whereby it may run partially as a channel in the instrument body or as a tube or pipeline. The media line 11 opens out in the forward end region of the treatment instrument 1, out of this, whereby the outlet opening 11a is directed towards the treatment site or to the tip of the tool 6.

With all exemplary embodiments of the invention, for which the same or similar parts are provided with the same reference signs, the handpiece 3 has a rotary part 12 mounted rotatably therein in a roller bearing. With the exemplary embodiment according to FIG. 1 there is involved one with an arc-shaped curved (FIG. 1) or angled (FIG. 2) shaft 13. This can be formed in one piece or consist of a rearward and a forward shaft section 13a, 13b, which are fixedly connected with one another at the beginning of the arc or at the apex of the angle. At the forward end of the shaft 13 there is located a thickened head 14 in which a receiving sleeve 18 is rotatably mounted, in which sleeve the tool 6 can be inserted with its shaft and can be releasably fixed in a manner known per se by means of a fixing device.

In the case of this treatment instrument 1, a drive motor 51, for example an electric motor, is arranged in the extended connection part 2, indicated by chain lines, and drivingly connected with the receiving sleeve 18 by means of a drive shaft or drive shaft train 53 having a plurality of drive shaft sections. In the region of the plug-in coupling 4 the drive shaft train 53 has a plug-in coupling 52 with two plug-in coupling elements 52a, 52b corresponding with one another in a form-fitting manner, whereby upon coupling and decoupling of the plug-in coupling 4 at the same time a coupling and decoupling of the plug-in coupling 52 is possible.

A drive shaft section 53a arranged in the rearward end region of the handpiece 3 extends up into the initial region of the curvature (FIG. 1) or the apex region of the angled (FIG. 3) shaft 13, whereby its forward end is connected with a third drive shaft section 53c by means of a second drive shaft section 53b extending, for example axially, in substance only in the curvature or involute or in the apex region, which third drive shaft section extends in the forward shaft section 13b up to the receiving sleeve 18 and is drivingly connected therewith. For connecting the drive shaft sections 53a, 53b, 53c there is provided in each case a gear transmission. At the forward end of the first drive shaft section 53a there is arranged a gear 54 having an internal toothing, which meshes with a pinion 55 at the rearward end of the second drive shaft section 53b. Thereby, the second drive shaft section 53b is arranged, with regard to the apex 13c, the angling or curvature, offset towards the side away from the tool 6, whereby on the forward end of the second drive shaft section 53b and on the rearward end of the third drive shaft section 53c there is arranged in each case a pinion 56, 57 in substance in a transverse plane or overlapping one another, in the sense of spur or conical gears which mesh with one another. The second and the third drive shaft section 53b, 53c include an obtuse angle W1, which is open towards the side away from the tool 6. The angle W2, which is included by the forward end region of the forward shaft section 13b and its rearward end region or the rearward shaft section 13a, is likewise obtuse.

The drive connection between the third drive shaft section 53c and the receiving sleeve 18 is formed by means of an angled gear transmission having a conical gear 58 at the forward end of the third drive shaft section 53c and conical gear 59 on the receiving sleeve 18. The tooth engagement between the conical gears 58, 59 is, with reference to the third drive shaft section 53c, arranged on its side away from the tool 6. Through this, the receiving sleeve 18 is driven in the same direction of rotation as the first drive shaft section 53a. The receiving sleeve 18 is rotatably mounted by means of two roller bearings 61, 62 (FIG. 2) in the head 14, which have a spacing from one another directed longitudinally of the axis of rotation 16, which spacing is larger than the conical gear 58, so that the latter can be arranged therebetween, including the conical gear 59, which is arranged on the side of the conical gear 58 away from the tool 6 and at the same time on the side of the roller bearing 61 towards the tool 6, and which is arranged further distant from the tool 6 than the other roller bearing 62. For rotary mounting of the second drive shaft section 53c there is arranged in each case a roller bearing 63, 64 (FIG. 2) on the end regions of this drive shaft section 53c, the outer rings of which are seated and mounted in a non-illustrated longitudinal hole of the shaft section 13b.

The configuration of the gear 54 as a hollow gear makes possible with radially small manner of construction, a relatively great gearing up of the speed of rotation between the first and the second drive shaft section 53a, 53b.

With the exemplary embodiment according to FIGS. 2 and 3 there are provided for mounting the first drive shaft section 53a and the second drive shaft section 53b in each case in the shaft 13, a two-row roller bearing 65, 66 in a bearing bush. This roller bearing 65, 66 is sufficient in each case to mount the entire drive shaft section 53a or 53b sufficiently stably. The first drive shaft section 53a projects beyond the roller bearing 65 freely outstanding rearwardly, whereby a slight radial flexibility is present for coupling with the drive shaft section 53d of the connection part 2. For increasing the flexibility there may be connected between the first drive shaft section 53a and gear 54 a joint connection 68 having a transverse pin 69, whereby the radial flexibility of the first drive shaft section 53a is increased. The gear 54 consists of a rearward cylindrical or hollow cylindrical mounting section 54a at the forward end of which a flange 54b is arranged which carries at its forward side a hollow gear crown 54.

The roller bearings 65, 66 may have two roller bearing inner rings 65b, 66b for example having an axial spacing from one another, or also one axially through-going roller bearing inner sleeve (not illustrated).

With the roller bearings 65, 66 the axial spacing of the roller rows from one another can be advantageously greater than the mean diameter of the roller body raceways. The roller bearing 66 is so long, see L, that it fits between the pinions 55, 56, whereby at the same time an axial restriction is constituted for the second drive shaft section 52b.

Both roller bearings 65, 66 are preferably mounted in a common carrier body 71 forming a bearing bush 23, which sits in the shaft 13 in the region of the rearward shaft section 13a neighbouring the apex point, is mountable from the rear and again dismountable from the rear, or vice versa, through a rearwardly or forwardly opening receiving hole 71a, and is axially fixable in the shaft section 13a.

For axial securing or positioning, there is associated with the roller bearing 66 in the bearing bush 23 a securing device 20 with at least one securing ring 24 of elastically deformable or elastically compressible material, which is arranged so deep in a ring groove 25 in the inner surface 23a of the bearing sleeve 23 that it projects beyond the inner surface 23a and thus forms a securing bead with which it sits in a ring groove 26, lying radially opposite to the ring groove 25, in the outer surface 66c of the roller bearing outer ring 66a. Preferably, the securing ring 24 presses with a, for example small, elastic biassing radially inwards against the base of the ring groove 26. This can be attained in that the inner diameter of the securing ring 24 is smaller than the inner diameter of the ring groove 26 and/or in that the half difference between the inner diameter of the ring groove 26 and the outer diameter of the ring groove 25 is somewhat smaller than the diameter of the securing ring 24, which is preferably round in cross-section. In both cases, the securing ring 24 is elastically biassed inwardly against the base of the ring groove 26. For improving the axial positioning it is also advantageous if the axial width of the ring grooves 25, 26 is somewhat smaller than the axial dimension of the securing ring 24, so that this is elastically compressed between the side walls or flanks 26a of the ring groove 25, 26. In the case of the exemplary embodiment, the cross-sectional form of the ring groove 25 is quadrilateral, and the cross-sectional form of the ring groove 26 is rounded in the form of a circular arc section. Other cross-sectional forms are however also possible.

For facilitating installation, the roller bearing 66 has at least on one end face a rounded or acute angled lead-in surface 27, which upon axial pushing in of the roller bearing 66 into the bearing bush 23 self-actingly elastically deforms and stretches the securing ring 24 and self-actingly springs this again into the ring groove 26 in the installed position. Preferably, a lead in surface 27 is provided at both end faces.

It is further advantageous to arrange the ring groove 26 axially offset with regard to the races of the roller bodies 22, through which material weakening of the roller bearing outer ring 66a is of lesser, or without, effect. Preferably the roller bearings 66 are similarly formed, so that the roller bearing 66 selectively fits to the one or to the other bearing position, e.g. in a position rotated by 180°.

If an axial securing of the roller bearing 66 is desired only in one axial direction, the ring groove 26 can be formed to run out axially to one side, as is shown per se by the exemplary embodiment according to FIG. 3 which is still to be described. With such a configuration, the flanks 26a of the ring groove 26 towards one another are adapted to the axial spacing of the securing rings 24 present and this preferably such that the securing rings 24 press with an elastic tension or compression against the preferably convergent flanks 26a.

As FIGS. 2 and 3 allow further to be recognised, in order to achieve an axially effective yieldability for the securing device 20 it is advantageous to arrange the associated roller bearing 66 in each case at an axial spacing from associated components of the head housing, so that the above-described axial yieldability is not restricted. If the axial yieldability is desired in only one axis direction, the roller bearing ring concerned can be restricted in the other axial direction by means of a bearing surface.

In the case of the exemplary embodiment, there are arranged two ring grooves 25, in each case with a securing ring 24, in the bearing bush 23, which for example are inwardly offset with reference to the roller bearing races.

As can be further understood from FIGS. 2 and 3, the rearward roller bearing 65 is in inserted from the rear into the receiving hole 71a of the carrier body 71 and for example by means of a flange 65b arranged at the rearward end of the outer bearing sleeve 65a axially fixed towards the fore. The forward roller bearing 66 is, in contrast, placed from the fore into a receiving hole 72 of the carrier body 71 and axially fixed or positioned by means of a securing device 20 with one or two securing rings 24. The flange forming the gear 54 is mounted in the receiving hole 71a between the roller bearing 65 and the bottom of the receiving hole 71a with play for movement. The outer ring 65a may be set up, by means of a securing device, corresponding to the securing device 20 according to FIG. 3 and rotated by 180°, against an unintended displacement to the rear, which is not illustrated in FIGS. 2 and 3.

With the configuration according to FIG. 3, however, the following special feature may be provided. On the one hand, the roller bearing outer ring, here the common outer mounting sleeve 66a, is positioned at one of its ends, here at its rearward end, at a shoulder 67 in the bearing bush 23, which shoulder may be formed by means of a step surface in the bore receiving the outer bearing sleeve 66a. Further, the at least one ring groove 26 is, upon abutment of the outer bearing sleeve 66a on the shoulder 67, offset towards the axial direction away from the shoulder 67, with regard to the associated ring groove 25, which can be clearly seen from FIG. 3. Through this offset, the securing ring 24 is non-symmetrically deformed with regard to its ring plane, whereby due to its elasticity its seeks to take its symmetrical form. Through this the securing ring 24 generates an axial force, see arrow 68, which elastically biasses the outer bearing sleeve 66a against the shoulder 67 and thus ensures its bearing on the shoulder 67.

A further advantage of the securing or positioning device 20 consists in that through the securing ring 24 a ring seal for the sealing off of the gap between the inner surface 23a and the bearing pin is formed, and in particular then when the securing ring 24 is elastically biassed not only against the bottom of the ring groove 26 but also against the bottom the ring groove 25.

81 designates a light conductor rod, which extends in the vicinity of the edge of the tool side of the shaft 13 in the shaft from the rear forwardly to the outlet window 82 directed towards the free end of the tool 6. In functional operation of this handpiece 3 light is coupled in from a light source 83 into the light conducting rod 81, whereby the light source 83 is arranged on a carousel 84 (schematically illustrated) rotatably mounted in or on connection part 2, which carousel is form-fittingly connected with the handpiece 13 by means of a carrier 13d, so that also in this case the free rotatability of the handpiece 3 in the plug-in/turn coupling 4 is ensured. The light conductor rod 81 and/or other media lines may run in an outwardly open longitudinal groove 73 in the carrier body 71. There may be arranged a plurality of longitudinal grooves 73 offset with respect to one another in the circumferential direction. In the region of the at least one longitudinal groove 73 the may be arranged in each case a longitudinal groove also in the flange 65c.

The securing device 20 in accordance with the invention may also be arranged between the inner ring 65b or 66b and the rotation part 12 concerned in a configuration corresponding to the above-described configurations.

The angle W3 included in FIGS. 1 and 2 between the middle axis of the forward shaft section 13b and the axis of rotation 16 of the receiving sleeve 18 is more than 90°, preferably substantially 100. Such a configuration is particularly favourable taking into account the anatomy in the mouth of a patient.

The rod-like handpiece 3 forms a grip part with the rearward grip or shaft section 13a, which preferably extends straight, and the forward grip or shaft section 13b adjoining thereon forwardly, which in accordance with FIG. 1 develops curved towards the side away from the insertion opening 5a. The curvature may be even, in particular in the form of a section of a circular arc, or may be formed to be digressive in the direction forwardly, i.e. the shaft section 13b may be more strongly curved in its rearward region than its forward region. The angular range W4 in which the curvature develops, may be about 10° to 28° in particular about 19°. The outer curvature radius r may be about 145 mm to 175 mm, in particular about 160 mm. The length of the curved shaft section 13b may be about the half of the overall length of the shaft 13. The middle axis 16 of the holder device 5 includes with the section of the curved middle axis 13e extending rearwardly from the intersection point, or with a tangent T touching the curved middle axis 13e at the intersection point, the angle W3. The intersection point between the middle axes 5a and 13e may lie at the forward end of the angle range W4 or may have an axial spacing x form the angle range W4.

The forward shaft section 13b may taper continuously forwardly, thereby uniformly or non-uniformly, e.g. digressively, so that its cross-sectional dimension y may be about 9 mm in the forward end region. In the rearward region of the forward shaft section 13b, the corresponding cross-sectional dimension z may be in substance 15.2 mm.

At least the forward shaft section 13b is constituted at its surface to be rough, to increase its gripability. For this purpose there may serve a microstructure 86 not illustrated in detail, the roughness depth of which is about 3 µm to 15 µm, preferably about 6 µm. The rough surface may be worked directly into the surface of the shaft section 13b, preferably of metal, e.g. corrosion resistant steel, in particular nickel silver, or it can be worked into the surface of a coating of the shaft section 13b.

In the above-described manner, also the shaft 13 overall may be constituted to be rough.

The shaft 13, with its sections 13a, 13b, may be constituted in one piece or two pieces. In the case of a two-piece configuration, the shaft sections 13a, 13b may be connected releasably, for example screwed together, with one another or non-releasably connected with one another.

With the exemplary embodiment according to FIG. 4, the receiving sleeve 18 in the head 14 is mounted in a two-row roller bearing 91, which has a through-going outer bearing sleeve 91a and two inner bearing sleeves 91b arranged at an axial spacing from one another. The forward drive shaft section 53c, with its forward conical gear 58, engages through the outer bearing sleeve 91a in a radial through-hole 92, and it meshes with the conical gear 59 arranged within the outer bearing sleeve 91a and between the inner bearing rings 91b. The latter conical gear is preferably arranged offset towards the side away from the insertion opening 5a so that it meshes with the conical gear 58 on its side away from the insertion opening 5a. In the case of the exemplary embodiment, the conical gear 59 is arranged, for example formed in one piece, on an end thickening 18a of the receiving sleeve 18. On the thickening 18a, which is formed at least in sections to be outwardly cylindrical, the inner bearing ring 91b of the associated roller body row can be mounted and preferably bear on a flange 18b of the thickening 18a with its end towards the insertion opening 5a, on which flange of the thickening there may also be formed the teeth on the side away from the inner bearing ring 19b. Between the middle axis 16 and the middle axis 13e or the tangent T, there is included the angle W3. The angle W3 may, however, also be about 90°, as is illustrated in FIG. 4. Within the scope of the invention it is also possible to arrange the conical gear 59 offset to the insertion hole 5a, so that it meshes with the conical gear 58 on its side towards the insertion opening 5a, which is not illustrated. The above-described variants with regard to the angle W3 and the position of the conical gear 59 may also alternatively be present in the case of the exemplary embodiments according to FIGS. 1 and 2.

In the case of the exemplary embodiment according to FIG. 4, there is arranged in the receiving sleeve 18, in its region towards the insertion opening 5a, a per se known clamping sleeve 18c having mutually opposite lying jaws 18d for the shaft of the tool 5. For releasing the tool 5, a release device 93 is arranged on the side away from the insertion opening 5a, having a release pin 93a which is axially displaceably mounted in the receiving sleeve 18 and can be pushed with a wedge 93b between the clamping jaws 18d. For actuation of the release pin 93a there is provided a push button 93c, which can be pushed in against the force of a compression spring 94 arranged covered by means of a flange of the push button 93c. The release device 93 with the push button 93c is arranged on a screw flange 95 which with a hollow cylindrical screw ring 95a can be screwed into a threaded hole of the head 14 and covers over a receiving hole 96 in which the outer bearing ring 91a is correspondingly pushed in from the side away from the insertion opening 5a and with its end towards the insertion opening 5a bears on an inner shoulder 14a of the head 14, and is thus axially bounded between the latter and the screw flange 95.

On the tool side of the head 14 there is screwed into the head 14 a screw flange 97 surrounding the receiving sleeve 18, which screw flange has one or more channels 98 arranged distributed around the circumference and directed at the treatment site, which channels start from a ring groove 99 in the head 14, which ring groove is connected with the media line 11. For sealing the ring groove 99 two concentrically arranged O-rings 101, 102 are arranged between the screw flange 97 and the head housing, in ring grooves which are preferably formed in the screw flange 97.

For securing the through-hole 92 in its position, there is provided for the outer bearing ring 91a a rotational securing means 103, which is preferably form-fittingly effective. In the case of the exemplary embodiment, the rotational securing means 103 is formed by means of an annex 103a on the circumference of the bearing outer ring 91a and a recess 104 in the wall of the head 14 which receives this annex. The recess 104 is formed as a slit running out towards the side away from the insertion opening 5a, so that the outer bearing sleeve 91a can be pushed in.

For its stabilisation, between the roller bearing rows the roller bearing outer ring 91a is preferably inwardly thickened.

In the claims:

1. Medical or dental medical handpiece having an elongate shaft, which has in a forward end region thereof a tool holder having a lateral insertion opening for a tool, and having a rearward shaft section and a forward shaft section which include an obtuse angle which is open to a side away from the insertion opening, in the shaft sections there being rotatably mounted in each case a drive shaft section, each of which stands in driving connection with one another by means of gears meshing with one another, and the forward shaft section standing in driving connection with the tool holder by means of gears meshing with one another, between the rearward drive shaft section and the forward drive shaft section there being arranged a middle drive shaft section, offset towards a side away from the insertion opening, a rearward gear of which meshes with a hollow gear crown of a forward gear of the rearward drive shaft section, the middle drive shaft being mounted in a roller bearing, a bearing bush disposed in the rearward shaft section, the bearing bush adapted to axially receive the roller bearing, and a securing device disposed on an inner surface of the bearing bush, the securing device positioning and securing the roller bearing within the bearing bush, the forward drive shaft section and the middle drive shaft section standing in driving connection with one another by means of pinion gears, wherein the pinion gears are in the form of spur or conical gears and the rearward gear of the forward drive shaft section, on its side away from the insertion opening, meshes with an associated gear of the middle drive shaft section, and the securing device comprises a securing ring.

2. Medical or dental medical handpiece according to claim 1, wherein the angle included between a middle axis of the insertion opening and a middle axis of the forward shaft section is greater than 90° and the forward gear of the forward drive shaft section meshes on its side away from the insertion opening with the gear of the tool holder.

3. Handpiece according to claim 1, wherein the forward shaft section is curved in an arc-shape towards the side away from the insertion opening.

4. Handpiece according to claim 3, wherein the curvature commences in the region of the middle drive shaft section or of the apex.

5. Handpiece according to claim 1, wherein the securing ring comprises an elastically deformable material.

6. Handpiece according to claim 1, wherein the inner surface of the bearing bush includes a ring groove adapted to at least partially receive the securing ring.

7. Handpiece according to claim 6, wherein a portion of the securing ring projects beyond the inner surface of the bearing bush, the portion forming a securing bead.

8. Handpiece according to claim 7, wherein an outer surface of the roller bearing includes a bead groove adapted to receive the securing bead.

* * * * *